(12) United States Patent
Radunsky et al.

(10) Patent No.: US 7,837,878 B2
(45) Date of Patent: *Nov. 23, 2010

(54) METHOD AND SYSTEM FOR COLLOID EXCHANGE THERAPY

(75) Inventors: David Radunsky, Dallas, TX (US); James R. Matson, Dallas, TX (US); Patrice A. Lee, Erie, CO (US)

(73) Assignee: Immunocept, L.L.C., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/425,895

(22) Filed: Apr. 17, 2009

(65) Prior Publication Data

US 2009/0204050 A1 Aug. 13, 2009

Related U.S. Application Data

(60) Continuation of application No. 11/387,556, filed on Mar. 23, 2006, now Pat. No. 7,520,992, which is a continuation of application No. 10/796,882, filed on Mar. 8, 2004, now Pat. No. 7,524,420, which is a division of application No. 09/858,210, filed on May 15, 2001, now Pat. No. 6,787,040.

(60) Provisional application No. 60/204,398, filed on May 16, 2000, provisional application No. 60/230,106, filed on Sep. 5, 2000.

(51) Int. Cl.
*B01D 61/00* (2006.01)
*A61K 38/38* (2006.01)

(52) U.S. Cl. ............... 210/645; 210/651; 424/130.1; 424/529; 604/5.01; 604/6.01; 604/6.09; 604/19; 530/362; 514/21; 514/776

(58) Field of Classification Search ............ 210/195.1, 210/195.2, 196, 198.1, 202, 203, 259, 321.6, 210/433.1, 434, 638, 639, 641, 645, 650, 210/651, 805; 424/529, 530, 130.1, 140.1; 604/5.01, 5.03, 6.01, 6.04, 6.09, 19, 27; 514/21, 514/776; 530/362, 363, 369

See application file for complete search history.

(56) References Cited

U.S. PATENT DOCUMENTS 4,191,182 A 3/1980 Popovich et al.

(Continued)

FOREIGN PATENT DOCUMENTS

CA 2495459 2/2004

(Continued)

OTHER PUBLICATIONS

Official Action in European Patent Application No. 02750294.7 dated Sep. 24, 2008 (3 pages).

(Continued)

*Primary Examiner*—Joseph W Drodge
(74) *Attorney, Agent, or Firm*—SNR Denton US LLP

(57) ABSTRACT

The present invention relates to a method and system for using a hemofilter to treat IMRD, hepatic failure, exogenous intoxication and other conditions associated with toxins in a patient's blood. One treatment includes the use of a very large pore hemofilter to remove target complex molecules and/or target molecules from a patient's blood and to infuse a replacement fluid into the patient's blood to maintain a prescribed albumin concentration in the patient's blood.

18 Claims, 2 Drawing Sheets

U.S. PATENT DOCUMENTS

| | | | |
|---|---|---|---|
| 4,229,291 A | | 10/1980 | Walch et al. |
| 4,350,156 A | | 9/1982 | Malchesky et al. |
| 4,350,594 A | * | 9/1982 | Kawai et al. ............... 210/637 |
| 4,402,940 A | * | 9/1983 | Nose et al. .................. 424/530 |
| RE31,688 E | | 9/1984 | Popovich et al. |
| 4,581,141 A | | 4/1986 | Ash |
| 4,648,974 A | | 3/1987 | Rosskopf et al. |
| 4,685,900 A | | 8/1987 | Honard et al. |
| 4,900,720 A | * | 2/1990 | Kotitschke .................. 514/21 |
| 4,966,709 A | | 10/1990 | Nose et al. |
| 5,571,418 A | * | 11/1996 | Lee et al. ..................... 210/651 |
| 5,744,042 A | * | 4/1998 | Stange et al. ............... 210/645 |
| 5,783,085 A | | 7/1998 | Fischel |
| 5,919,444 A | | 7/1999 | Norman, Jr. |
| 6,008,199 A | | 12/1999 | Grinnell et al. |
| 6,231,536 B1 | | 5/2001 | Lentz |
| 6,287,516 B1 | * | 9/2001 | Matson et al. ................. 422/44 |
| 6,342,157 B1 | | 1/2002 | Hood |
| 6,736,972 B1 | | 5/2004 | Matson |
| 6,787,040 B2 | * | 9/2004 | Radunsky et al. ........... 210/651 |
| 7,291,122 B2 | | 11/2007 | Matson |
| 7,520,992 B2 | * | 4/2009 | Radunsky et al. ........... 210/645 |
| 7,524,420 B2 | * | 4/2009 | Radunsky et al. ........... 210/645 |
| 2001/0051106 A1 | | 12/2001 | Matson |
| 2004/0060866 A1 | | 4/2004 | Radunsky et al. |
| 2004/0173530 A1 | | 9/2004 | Radunsky et al. |
| 2009/0204050 A1 | | 8/2009 | Radunsky et al. |

FOREIGN PATENT DOCUMENTS

| | | |
|---|---|---|
| EP | 787500 A1 | 8/1997 |
| EP | 0739234 | 2/2003 |
| WO | WO 2004/014315 | 2/2004 |
| WO | WO 2004/056460 | 7/2004 |
| WO | WO 2004/112869 | 12/2004 |

OTHER PUBLICATIONS

Bellomo et al., "Extracorporeal blood treatment (EBT) methods in SIRS/Sepsis"; The International Journal Of Artificial Organs, 2005, vol. 28, No. 5, pp. 450-458.

Bellomo et al., "Hemofiltration and Hemoperfusion on Sepsis and Septic Shock," Acute Dialysis Quality Initiative, 3rd International Consensus Conference, Workgroup 1 (2003) (Date of Conference obtained from ADQI Newsletter found at www.adqi.net/#background).

Bellomo et al.; "An Introduction to Continuous Renal Replacement Therapy", Atlas of Hemofiltration, p. 1-9, 2002.

Chung et al., "Continuous venovenous hemofiltration in severely burned patients with acute kidney injury: a cohort study", Critical Care 2009, 13:R62 (doi: 10.1186/cc7801) (Available online at http://ccforum.com/content/13/3/R62).

Colton, "Analysis of Membrane Processes for Blood Purification," In-Depth Review 5:202-251 (1987).

Fong et al., "Endotoxemia Elicits Increased Circulating βIFN/IL-6 In Man," Journal of Immunology vol. 142, 2321-2324, No. 7 (Apr. 1989).

Frigon et al., "Hemofilter Solute Sieving Is Not Governed by Dynamically Polarized Protein," Trans Am. Soc. Artif. Intern, Organs vol. XXX (1984).

Harris et al., "Manifestations of Sepsis" arch. Intern. Med. vol. 147 (Nov. 1987).

Hinshaw et al. "Extracorporeal Perfusion Without, Exogenous Anticoagulations: Its Protective Role in Endotoxin Shock" Circulatory Shock 9:281-295 (1982).

Hinshaw et al., "Staphylococcus Aureus-Induced Shock: A Pathyphysiologic Study" Circulatory Shock 26:257-265 (1988).

Honore et al., "Extracorporeal removal for sepsis: Acting at the tissue level—The beginning of a new era for this treatment modality in septic shock", Crit Care Med 2004, Vo. 32, No. 3 (pp. 896-897).

Honore et al., "High Volume and High Permeability Haemofiltration for sepsis: the evidence and the key issues", Care of the Critically Ill, Jun. 2003, vol. 19, No. 3.

Honore et al., "Prospective evaluation of short-term, high-volume isovolemic hemofiltration on the homodynamic course and outcome in patients with intractable circulatory failure resulting from septic shock", Crit. Care Med 2000 vol. 28, No. 11, pp. 3581-3587.

Honore et al.; "Hemofiltration, absorption, sieving and the challenge of sepsis therapy design", Critical Care, Oct. 2006, vol. 6, No. 5.

Honore et al.; "Short-Term High-Volume Hemofiltration in Sepsis: Perhaps the Right Way Is to Start With . . . ", Letters to the Editor, Crit Care Med 2002, vol. 20, No. 7 (pp. 1673-1677).

Lee et al., "Effects of filter pore size on efficacy of continuous arteriovenous hemofiltration therapy for Staphylococcus aures-induced septicemia in immature swine", Crit Care Med 1998, vol. 26, No. 4 (pp. 730-737).

Lee et al., "Continuous Arteriovenouse Hemofiltration (CAVH) Therapy for Sepsis-Induced Acute Lung Injury in Immature Swine", FASEB J., 1990 4(4) SUPPL: A953.

Leypoldt, et al., "Dextran Sieving Coefficients of Hemofiltration Membranes" Trans. Am. Soc. Artif. Inter. Organs vol. XXX (1983).

Matson et al.; "Evolving concepts of therapy for sepsis and septic shock and the sue of hypermeable membranes", Curr Opin Crit Care 2000, 6:432-436.

Matson et al; "Blood filtration: new opportunities and the implications of systems biology", Critical Care and resuscitation 2004; 6:207-207.

Michie et al., "Detection of Circulating Tumor Necrosis Factor After Endotoxin Administration," New Eng. Journal of Medicine 318:1481-1486 (Jun. 1988).

Parsonett et al., "Induction of Interleukin-1 by Strains of Staphylococcus arueus from Patients with Nonmenstrual Toxic Shock Syndrome", Journal of Infectious Diseases 124:1 (Jul. 1986).

Sheagren, "Staphylococcus areus The Persistent Pathogen" New Eng. Journal of Medicine 310:21 (May 1984).

Shumak and Rock, "Therapeutic Plasma Exchange" New Eng. Journal of Medicine 213:12 (Mar. 1984).

Sporn, et al. "Continuous Pump Driven Hemofiltration (CPDHF) in Septic Renal Failure," First Vienna Shock Forum, Part B: Monitoring and Treatment of Shock, pp. 225-233 (1987).

Todd et al., "Recovery From Endotoxin Shock After Extracorporeal Perfusion Without Anticoagulation," Circulatory Shock 6:261-269 (1979).

Weinstein et al., "The Clinical Significance of Positive Blood Cultures: A Comprehensive Analysis of 500 Episodes of Bacteremia and Fungemia in Influencing Prognosis" Reviews of Infectious Disease 5:1 (Jan.-Feb. 1983).

F. Coraim; R. Fasol; F. Stellwag; E. Wolner; Continuous Arteriovenous Hemofiltration (CAVH) After Cardiac Surgery; Clinic for Anesthesia and General Intensive Care Medicine and 2nd Surgical Clinic, University of Vienna Austria. Continuous Arteriovenous Hemofiltration (CAVH); Int. conf. on CAVH, Aachen 1984, pp. 116-124 (Karger, Basel 1985). (9 pages).

W.F. Koller; H.M. Benzer; G.F. Pauser; CAVH in Acute Respiratory Failure; Research Center for Intensive Care medicine, 2$^{nd}$ Surgical Clinic, University of Vienna, Vienna, Austria; Continuous Arteriovenous Hemofiltration (CAVH); Int. Conf. on CAVH, Aachen 1984; pp. 96-102 (Karger, Basel 1985). (7 pages).

G. Zobel; E. Ring; M. Kutting; H.M. Grubbauer; Five years experience with continuous extracorporeal renal support in paediatric intensive care; (Received 1990; Accepted Feb. 3, 1991; Department of Paediatrics, University of Graz, Austria); Intensive Care Medicine; 1993 17:315-319. (5 pages).

Patrice A. Lee PhD; James R. Matson, MD; Robert W. Pryor, MD, FCCM; Lerner B. Hinshaw, PhD, FCCM; Continuous arteriovenous hemofiltration therapy for Staphylococcus aureus-induced septicemia in immature swine; Critical Care Medicine 1993; vol. 21, No. 6. (11 pages).

Non-final Office Action date mailed Sep. 29, 2008 for U.S. Appl. No. 11/934,978.

Response filed Mar. 30, 2009 for U.S. Appl. No. 11/934,978.

* cited by examiner

METHOD AND SYSTEM FOR COLLOID EXCHANGE THERAPY

RELATED APPLICATIONS

This application is a continuation of, and therefore claims priority from, U.S. patent application Ser. No. 11/387,556 entitled METHOD AND SYSTEM FOR COLLOID EXCHANGE THERAPY filed on Mar. 23, 2006 in the name of David Radunsky, James R. Matson and Patrice A. Lee, assigned U.S. Pat. No. 7,520,992, which is a continuation of U.S. Divisional patent application Ser. No. 10/796,882 filed Mar. 8, 2004 entitled METHOD AND SYSTEM FOR COLLOID EXCHANGE THERAPY, assigned U.S. Pat. No. 7,524,420, which is a divisional of U.S. patent application Ser. No. 09/858,210 filed May 15, 2001, and entitled METHOD AND SYSTEM FOR COLLOID EXCHANGE THERAPY, now U.S. Pat. No. 6,787,040 which claims priority from provisional application Ser. No. 60/204,398, filed on May 16, 2000 and provisional application Ser. No. 60/230,106, filed on Sep. 5, 2000, both provisional applications having the title of METHOD AND SYSTEM FOR COLLOID EXCHANGE THERAPY; each of the above-referenced patent applications is hereby incorporated herein by reference in its entirety.

TECHNICAL FIELD

The present invention relates generally to systems, methods, and devices used for hemofiltration. More specifically, the present invention relates to very large pore hemofiltration ("VLPH") for treating liver failure, for treating exogenous toxin exposures, and for treating inflammatory mediator-related diseases ("IMRD") including sepsis and septic shock, which include systemic inflammatory response syndrome ("SIRS"), multiorgan system dysfunction syndrome ("MODS"), multiorgan system failure ("MOSF"), and compensatory anti-inflammatory response syndrome ("CARS"), and for treating other conditions associated with toxin circulating in a patient's blood.

BACKGROUND OF THE INVENTION

Discussed herein are three subjects. First, devices and procedures for the therapeutic manipulation of target receptor molecules, target complex molecules, and target molecules in immune mediator related disease, and hepatic failure, and exogenous intoxication. Second, selected physiologic roles of albumin in health, immune mediator related disease, hepatic failure and exogenous intoxication, in particular effects of oncotic pressure and binding of physiologic or pathologic molecules. Third, the physiologic roles of soluble receptor and carrier molecules with respect to pro- and anti-inflammatory mediators ("IM") in particular and toxins in general.

Medical Blood Filtration: Treatment of certain diseases by filtration of blood is well established medical practice. Dialysis, using dialysis filters, which remove molecules with molecular weights up to 5,000 to 10,000 Dalton, is used to treat chronic and some acute renal failure. Conventional hemofiltration, discussed below, is used to treat acute renal failure, and in some cases, chronic renal failure. Plasmapheresis, using plasma filters or centrifuge techniques which remove molecules with molecular weights of 1,000,000 to 5,000,000 Dalton or more, is used to treat diseases associated with high molecular weight pathologic immunoglobulins or immune complexes, (e.g., multiple myeloma, lupus vasculitis, etc.).

Conventional hemofilters are well known medical devices commonly used to filter the blood of a patient with acute renal failure, and in some cases, chronic renal failure. The hemofilter may be used either for convective or dialytic depuration of blood. Many hemofilters are on the market with various characteristics. However, conventionally they all share one major characteristic, which is a nominal or effective molecular weight cutoff of less than 69,000 Dalton—the molecular weight of albumin. Conventional hemofilters are generally designed to minimize or avoid sieving of albumin. The reason is that the removal of albumin in the application of renal failure treatment is of no benefit, and would be a deleterious side effect, because the oncotic pressure of plasma would be reduced and edema promoted. Albumin could be replaced, but would add cost and risk with no therapeutic benefit. Therefore, conventional hemofilters are designed to avoid sieving of albumin.

Plasmapheresis has the objective of sieving all plasma proteins, especially all classes of immunoglobulins and immune complexes. This requires a molecular weight cutoff of from 1 million to 5 million Dalton, or more. Plasmapheresis membranes are designed to reject only cellular elements of blood, and are the most extreme of the blood filtration techniques designed to produce an acellular filtrate.

Physiology of Albumin and Soluble Receptor and Carrier Molecules:

Serum albumin serves a number of vital functions, two of these are its oncotic function and its chemical binding and transport of both physiologic and pathologic molecules. Albumin provides 80% of the oncotic pressure of plasma. This oncotic pressure keeps plasma water within the blood-vascular space, preserving the plasma water component of the blood volume, and preventing tissue edema by drawing tissue fluid back into the plasma from tissue. Albumin normally is present in human plasma at a concentration of about 3.5 to 5.0 gm/100 ml. If albumin concentration declines, typically to a concentration of <2.5 gm/100 ml, then oncotic pressure drops below its critical level, and edema fluid accumulates in tissues, body cavities (e.g., ascites, pleural effusion), and in air spaces in the lung (e.g., pulmonary edema). This accumulation of edema fluid may result in vital organ dysfunction, increased susceptibility to infection, and hyper-coagulable states. Thus, depletion of albumin molecules to the extent that oncotic pressure is excessively reduced is to be avoided.

The chemical binding and transport functions of albumin are numerous. In most cases, potentially biologically active molecules in the blood circulation only have their biologic effects when they are free in suspension or solution in the plasma water. In this free state, the molecule is able to interact with its receptor(s) to bring about biologic effects. Such biologic actions may be agonistic or antagonistic. Binding of a potentially biologically active molecule to albumin or other carrier or soluble receptor molecule usually inactivates the molecule by preventing combination with its tissue receptor. In some instances, the binding functions are part of normal physiologic process. For example when albumin binds calcium or magnesium ions, it is a dynamic process that helps to preserve the proper concentration of ionized calcium in the plasma water. If ionized calcium drops, calcium is released from albumin to restore normal plasma water ionized calcium. In other instances, the binding function of albumin and other receptor molecules protects against disease causing molecules by participating in their inactivation and detoxification.

Another major function of albumin is its role in detoxification, in which it binds endogenous or exogenous toxins. In this role, albumin acts both to detoxify the toxin by binding and therefore inactivating it, and also as a carrier molecule, transporting the toxic molecule to the liver for chemical transformation (detoxification) and excretion, or to the kidney for excretion. Endogenous toxins arise from a great many pathologic bodily processes. During sepsis and septic shock, inflammatory mediators ("IM") are produced in excess. At the site of local tissue injury or infection, IM serve the vital immune functions of removal and healing of injured or dead tissue, or resisting or destroying infecting organisms. When IM become excessive and spill over into the general circulation, they may become toxic to the body causing the systemic inflammatory response syndrome, with complicating multiorgan dysfunction syndrome and multiorgan system failure. These IM are carried in the plasma bound to albumin, bound to other receptor molecules, or free in plasma water. Binding by albumin and other receptor molecules moderates and ablates the effects of circulating IM. When the binding capacity is exceeded, the circulating IM become much more toxic and the moderating effects of albumin-carrier molecule binding are exceeded.

Other diseases, such as rheumatoid arthritis, pemphigoid vulgaris, multiple sclerosis, lupus, graft versus host disease and similar conditions, are similarly caused by excess circulating IM. These conditions generally result from an autoimmune process in which IM, either physiologic or pathologic, are dysfunctionally produced and are therefore toxic in any amount, or produced in dysfunctionally large and toxic quantities. Sepsis-septic shock and the autoimmune diseases, each resulting from dysfunctional and/or dysfunctionally abundant IM, may be referred to in aggregate as Inflammatory Mediator Related Disease ("IMRD").

Liver failure is a complex disorder with an intricate pathophysiology and diverse effects on many vital organs. It is characterized by the accumulation in the body of many toxins that arise from body metabolic processes, which, under normal conditions, are quickly detoxified and eliminated by the liver, but which, in liver failure, accumulate in the body. The pathologic effects of liver failure are varied and include bleeding (failure of liver to produce clotting factors), infection (failure of liver to remove organisms translocated from the gut into the portal circulation), and the accumulation, as noted above, of various liver failure toxic substances which have been only partially characterized. The lethal effect of these liver failure toxic substances is hepatic coma with progressive cerebral edema and eventual brain stem herniation and death. Liver failure toxic substances are extensively bound by albumin. While several supportive therapies are in use to reduce these toxic substances and ameliorate the effects of hepatic failure, none have shown a clear or consistent benefit.

Exogenous toxin exposures such as suicide attempts, accidental toxin ingestions and environmental (industrial, agricultural, etc.) toxin exposures are of great diversity. The majority of these exogenous toxins are bound to albumin and other tissues, thus excretion by natural means (kidney elimination) or artificial means (dialysis) is severely limited. Therapy for nearly all these intoxications is supportive only. In most intoxications, which are mild or moderate, simple supportive care and allowing the body's own detoxification mechanisms time to work, is satisfactory. However, in severe intoxications, particularly with more dangerous chemicals (e.g., tricyclic antidepressants, aspirin, etc) removal by some extracorporeal means would be desirable. However, current methods are not adequate to overcome binding of exogenous toxins to albumin or tissue and remove them from the body.

Not all carrier molecules inhibit the function of the bound molecule; in some cases, biologic activity of the bound molecule is enhanced by binding to a carrier molecule. For example, lipopolysaccharide (endotoxin) stimulation of cyotkine production is enhanced by low levels of lipopolysaccharide binding protein (LBP). LBP is an acute phase carrier protein made by the liver.

SUMMARY OF THE INVENTION

In accordance with teachings of the present invention, a method and system for a new type of hemofiltration referred to as very large pore hemofiltration ("VLPH") is provided. Very large pore hemofiltration includes sustained removal of albumin and similar large receptor molecules and carrier molecules for the purpose of removing both bound and unbound pathologic molecules or toxins. U.S. Pat. No. 5,571,418 teaches the use of a hemofilter with a nominal molecular weight cutoff of 100 to 150 kiloDalton (1,000 Daltons=1 kiloDalton) for the treatment of sepsis, septic shock, and other conditions. The purpose of the filter in the '418 patent is to remove circulating IM. A 100-kiloDalton hemofilter may initially sieve small amounts of albumin, but even if it does, albumin sieving quickly becomes negligible due to membrane polarization soon after the procedure begins.

Membrane polarization is well recognized in filtration process of blood and consists of the accumulation of a protein layer or "cake" on the membrane surface which characteristically reduces its sieving capacity (e.g., effective molecular weight cutoff) by 30 to 50%. The application of the 100 kD filter accepts the possibility of minor albumin sieving as a side effect of its therapeutic application. Therefore, a very large pore hemofiltration membrane suitable for the therapy of the present invention often requires a nominal molecular weight cutoff of >100 kD. Hemofilters with a nominal molecular weight cutoff <100 kiloDalton are generally not capable of sustained effective removal of albumin, and large receptor and carrier molecules, especially when target molecules are bound to them.

VLPH is distinct from plasmapheresis in the following critical ways. First, VLPH seeks sieving of proteins such as albumin, soluble tumor necrosis factor receptor 75 (molecular weight=75,000 Dalton), and similar soluble receptor and carrier molecules for the reasons stated above. VLPH specifically avoids removal of significant amounts of immunoglobulins and similar large molecules because removal of these molecules is associated with a marked increase in the risk of opportunistic infection.

Inflammatory mediator related disease ("IMRD"), liver failure, exogenous intoxication, and other conditions associated with toxins circulating in the blood are similar in that each is a severe pathologic process, often acutely life threatening, and in need of urgent or emergent therapy. Therefore, VLPH should generally be most effective when initial high volumes of ultrafiltrate are removed (exchanged for replacement fluid) for limited periods of time. Thus, the present invention will often be most effective at initial adult patient ultrafiltration rates of from 2-5 liters/hour, or even up to 15 to 20 liters/hour or more, and for initial treatment times ranging from about 4-10 hours, but generally not more than 24 hours at a time. Conventional hemofiltration produces ultrafiltration rates of about 1-2 liters/hour and is used on a continuous basis over a few to several days.

Devices and procedures, incorporating teachings of the present invention, fulfill longstanding needs for an effective therapy to treat IMRD, liver failure, exogenous toxin exposure and other conditions associated with toxins in the blood by removing target molecules and target complex molecules from a patient's blood. Such devices and procedures may be generally described as plasma colloid exchange therapy (PCET).

BRIEF DESCRIPTION OF THE DRAWINGS

A more complete and thorough understanding of the present invention and advantages thereof may be acquired by referring to the following description taken in conjunction with the accompanying drawings, in which like reference numbers indicate like features, and wherein.

DETAILED DESCRIPTION OF SPECIFIC EMBODIMENTS

Figure 1:
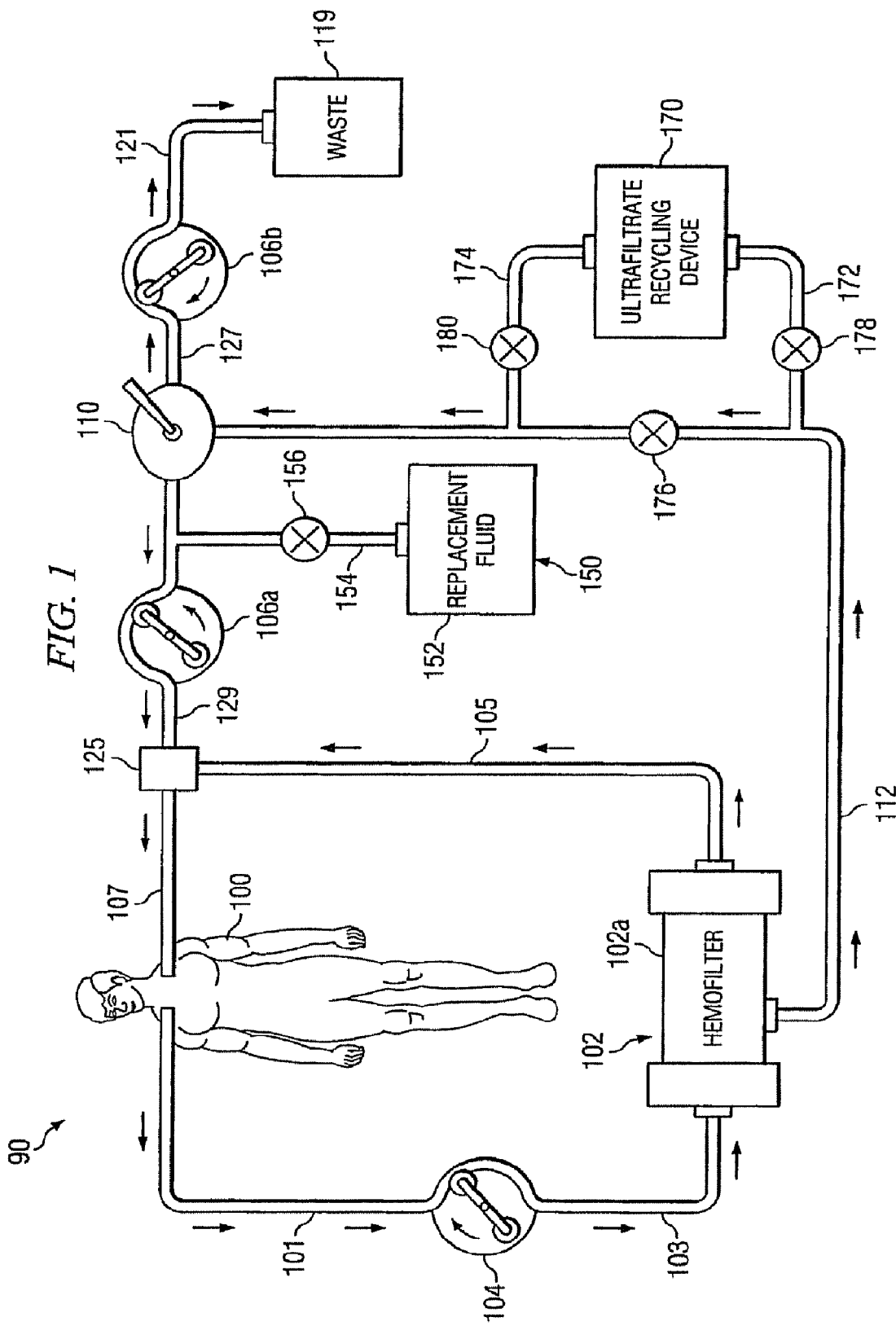
FIG. 1 is a schematic diagram showing one example of a very large pore hemofiltration system incorporating teachings of the present invention.
Figure 2:
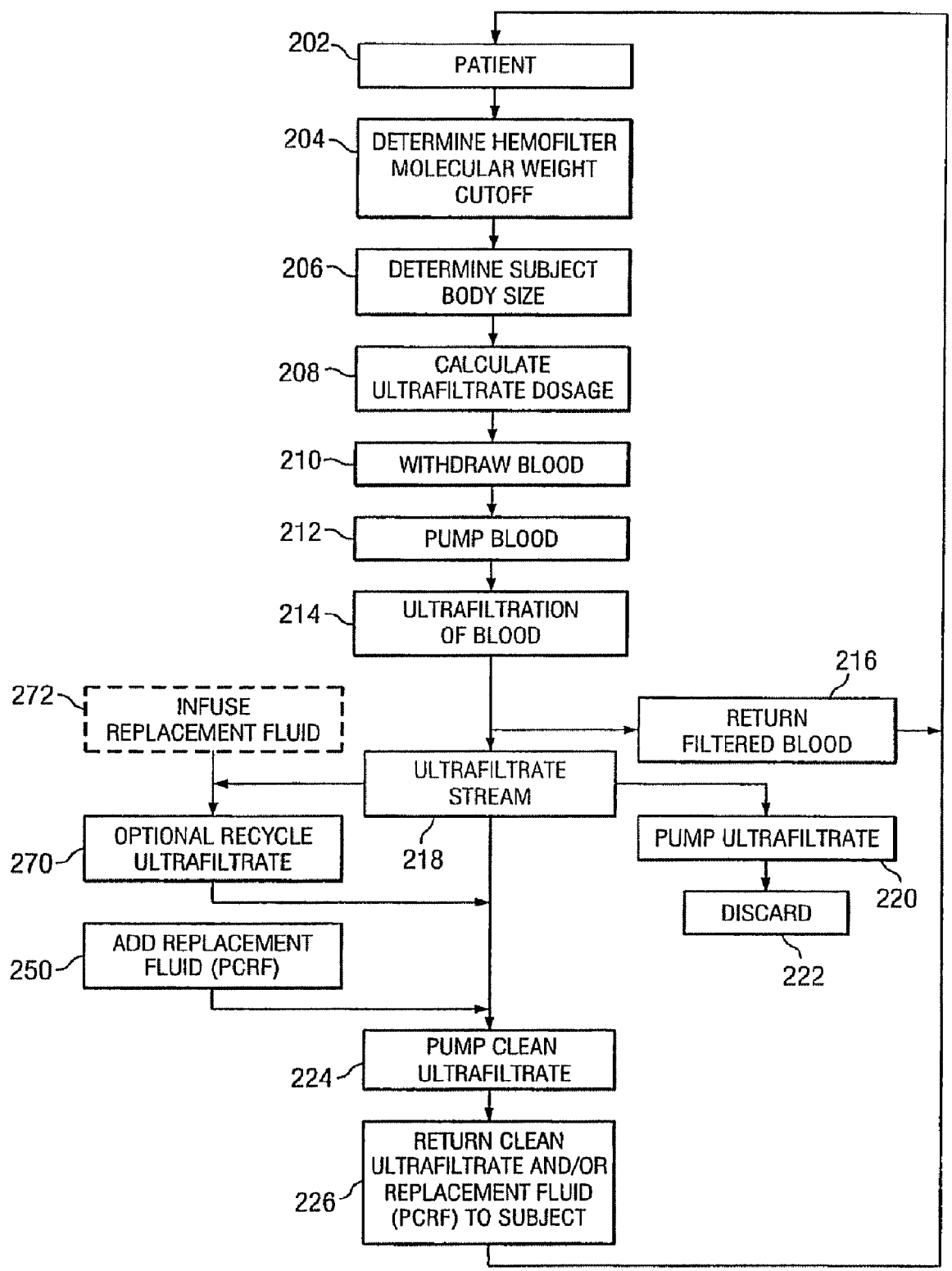
FIG. 2 is a block diagram showing one example of a method for treating a wide variety of conditions associated with inflammatory mediators and bound or unbound toxins in a patient's blood in accordance with teachings of the present invention using a hemofiltration system, replacement fluid for ultrafiltrate discarded from the hemofiltration system and an optional ultrafiltrate recycling device.

Preferred embodiments of the invention and its advantages are best understood by reference to FIGS. 1 and 2.

For purposes of this patent application, albumin, receptor molecules, and carrier molecules will be referred to collectively as "target receptor molecules". A wide variety of naturally occurring receptor molecules and carrier molecules may be satisfactorily used with this invention. Also, receptor molecules and carrier molecules may be designed and artificially created to bind with specific target molecules or general classes of target molecules. The term "clean target receptor molecule" refers to a receptor molecule or a carrier molecule which is not contaminated with or bound with a target molecule. The term "clean albumin" refers to albumin which is not contaminated with or bound with a target molecule.

For purposes of this patent application, albumin with bound IM and/or toxins, receptor molecules with bound IM and/or toxin, and carrier molecules with bound IM and/or toxin, will be referred to collectively as "target complex molecules". For purposes of this patent application, unbound IM, and unbound toxin (whether endogenous or exogenous) will be referred to collectively as "target molecules." Endogenous toxins include but are not limited to IM, liver failure related toxins, and metabolites of certain exogenous toxins. Exogenous toxins include chemicals such as medicine taken in excess, industrial and/or agricultural chemical exposures, and the like.

Various embodiments of the present invention include a process, method, and system to treat IMRD, to treat hepatic failure and coma, to treat exogenous intoxication, and/or to treat other conditions associated with bound and unbound toxins in a patient's blood including target molecules and target complex molecules.

One example of a very large pore hemofiltration (VLPH) system incorporating teachings of the present invention is shown in FIG. 1. System 90 may be used to treat mammals such as patient 100. System 90 may include a very large pore hemofilter 102, blood lines 101, 103, 105, 107 and ultrafiltrate lines 112, 127 and 121, source 150 of replacement fluid and optional ultrafiltrate recycling device 170. System 90 represents only one example of an extracorporeal blood circuit which may be used to treat patients in accordance with teachings of the present invention. For example, ultrafiltrate recycling device 170 may not be included in some systems used to treat a patient using hemofilter 102. For other systems, ultrafiltrate may flow directly from hemofilter 102 to waste reservoir 119.

Very large pore hemofilter 102 receives a stream of blood from patient or mammal 100 and removes ultrafiltrate from the stream of blood and thereby creates a stream of filtered blood and a stream of ultrafiltrate flowing through tubing 112. The filtered blood is preferably returned to patient 100. All or portions of the ultrafiltrate may be discarded to waste reservoir 119. Alternatively, all or portions of the ultrafiltrate may be cleaned and returned to patient 100.

Very large pore hemofilter 102 preferably sieves the ultrafiltrate from the blood stream. The ultrafiltrate will typically include a fraction of plasma water, electrolytes, peptides, proteins, target receptor molecules, target complex molecules, and target molecules. The sieved target molecules, target receptor molecules, and target complex molecules generally have a molecular size smaller than the nominal or effective pore size of the VLPH membrane (not expressly shown).

Very large pore hemofilter 102 is preferably formed from one or more biocompatible materials. In particular, very large pore hemofilter 102 may include a membrane disposed within case 102a. The membrane may be formed from the group of biocompatible materials (e.g., polysulfone, polyacrylonitrile, polymethylmethacrylate, polyvinyl-alcohol, polyamide, polycarbonate, etc.) and biocompatible cellulose derivatives. The case may be formed from polycarbonate or some other suitable biocompatible material. The VLPH membrane will generally remove albumin from the patient's blood. Depletion of albumin below acceptable levels will occur unless plasma colloid replacement fluid (described below) is provided in accordance with teachings of the present invention.

Various types of membranes may be used. Examples of such membranes include either a parallel plate or hollow fiber format. The membrane material may be any biocompatible material, typically polysulfone, polyacrylonitrile, polymethylmethacrylate, polyvinylalcohol, polyamide, polycarbonate, cellulose derivatives, and the like. The effective molecular weight cutoff will allow for effective sieving of target receptor molecules, target complex molecules, and target molecules, even after the membrane has undergone membrane polarization. The purpose of the membrane is to efficiently remove target receptor molecules, target complex molecules, and target molecules, as well as associated plasma water and associated solutes. The size and other sieving characteristics of albumin or other target receptor molecules may change when bound with various target molecules.

For the embodiment represented by system 90, first tubing 101 interfaces with patient 100 and blood pump 104. Blood pump 104 controls the flow of blood from patient 100. Blood exits from blood pump 104 through second tubing 103 and flows to hemofilter 102. Hemofilter 102 further interfaces with third tubing 105 and ultrafiltrate tubing 112. Filtered blood exiting hemofilter 102 through third tubing 105 flows to three-way joint 125 and fourth tubing 107 where it returns to patient 100.

Ultrafiltrate removed from the blood stream supplied by blood pump 104 to hemofilter 102 may flow through ultrafiltrate tubing 112 to three-way joint or three way valve 110 where the ultrafiltrate stream is discarded. Ultrafiltrate entering three-way joint 110 may be discarded through ultrafiltrate tubing 127, ultrafiltrate pump 106b, and discard ultrafiltrate tubing 121 to waste reservoir 119.

For some applications, ultrafiltrate recycling device 170 may be coupled with ultrafiltrate tubing 112 by tubing 172 and tubing 174. Ultrafiltrate recycling device 170 may include an adsorptive filter or other device operable to form clean ultrafiltrate by removing target molecules and target complex molecules from the ultrafiltrate. Control valve 176 may be disposed in ultrafiltrate tubing 112 between the respective junctions with tubing 172 and tubing 174. One or more control valves 178 and 180 may also be disposed in tubings 172 and 174 between ultrafiltrate recycling device 170 and ultrafiltrate tubing 112. For some treatment therapies, control valve 176 may be opened and control valves 178 and/or 180 closed so that all of the ultrafiltrate stream will flow from hemofilter 102 through tubing 112 to three-way joint 110 to waste reservoir 119. For other treatment therapies, control valve 176 may be closed and control valves 178 and 180 opened to direct the ultrafiltrate stream from hemofilter 102 through ultrafiltrate recycling device 170.

All or a selected portion of clean ultrafiltrate from ultrafiltrate recycling device 170 entering three-way joint 110 may be directed to ultrafiltrate return pump 106a and return ultrafiltrate tubing 129. The clean ultrafiltrate may flow through three-way joint 125 and tubing 107 to patient 100 along with the filtered blood stream. All or selected portions of clean ultrafiltrate may be directed from three-way joint 110 to waste reservoir 119.

The rate of blood flowing through blood pump 104 and the total amount of blood circulated through hemofilter 102 will depend on the condition of patient 100, the molecular weight cutoff of the associated hemofilter membrane, the body size of patient 100, and other requirements for effective treatment of the patient. The amount of blood, the blood flow rate and the duration of treatment are preferably determined on a case by case basis after factoring the weight, the age and the nature and severity of illness of patient 100. Often, blood flow rates may range from one hundred to two hundred milliliters/minute. Typically, total ultrafiltrate flow rate may range between one to nine liters per hour of which from zero to nine liters per hour may be discarded. The discard rate will be determined by the fluid balance requirements of patient 100 and the need for fluid removal. All clean ultrafiltrate not discarded may be returned to patient 100. The use of replacement fluid will be discussed later in more detail.

The composition of the material making up the blood pump, ultrafiltrate pumps, replacement fluid reservoir, tubing, ultrafiltrate tubing and ultrafiltrate recycling device is preferably a biocompatible material, such as polyvinylchloride, but not limited to this material. The tubing may be flexible and have dimensions complementary with associated hemofilter connections, ultrafiltrate recycling device connections, replacement fluid reservoir connection, joints, stop cocks, or pump heads.

Ultrafiltrate waste pump 106b may be used to pump a portion or all of the ultrafiltrate to waste reservoir 119. Ultrafiltrate return pump 106a may be used to pump a portion or all of the recycled or clean ultrafiltrate back to patient 100. Ultrafiltrate return pump 106a may also be used to infuse replacement fluid into patient 100. Tubing 107 transfers filtered blood along with replacement fluid and/or recycled ultrafiltrate or clean ultrafiltrate (if recycling is being done) to patient 100. Tubing 129 transfers recycled or clean ultrafiltrate and replacement fluid from the ultrafiltrate return pump 106a. The various pumps are all optional so long as sufficient blood circuit pressure and flow are provided. Use of ultrafiltrate recycling device 170, and apportionment of ultrafiltrate to recycling and return to patient 100 or to waste reservoir 119 is operator dependent.

Examples of Very Large Pore Hemofiltration and Plasma Colloid Exchange Therapy.

For use in IMRD, liver failure, exogenous intoxications and other conditions associated with toxins in the blood, the present invention teaches a very large pore hemofilter with a membrane capable of sieving a significant amount of target molecules, target receptor molecules, and target complex molecules over a significant portion of the therapy time. The very large pore hemofilter will typically have a sieving capacity sufficient to provide for an appropriately rapid exchange of target complex molecules that are circulating in plasma, and removing target molecules located in tissues.

Now referring to FIG. 2, a flow diagram showing one method for determining hemofiltration treatment dosage according to teachings of the present invention is provided. The treatment method includes determining the medical condition of patient 100 at step 202 and molecular weight cutoff for hemofilter 102 at step 204. In one embodiment, a hemofilter may be used based on the nominal molecular weight cutoff, or another specific expression of the molecules that are sievable by the associated membrane. A hemofilter may also be selected based on membrane surface area and membrane material.

The method further includes determining patient 100's body size 206. Determining body size may include measuring the body surface area, weight, mass, or lean body mass of patient 100. Alternatively, measuring body size may include using other unambiguous, commonly used measure to account for patient 100's body size. The ultrafiltrate dosage is then calculated using subject body size and the hemofilter molecular weight cutoff. In one embodiment the dosage will stipulate filter blood flow/unit body size/unit time. Body size may be stated as surface area, body weight, body mass, lean body mass or any other unambiguous measure. Time may be measured in minutes, hours, or another suitable measure.

The dose of ultrafiltrate volume remove from patient 100 may be indexed to body size and time. Specifically, the volume of ultrafiltrate per unit of body size per unit time may be determined. Volume of ultrafiltrate may be stated in liters, milliliters, or another suitable volume measure. Body size may be stated in kilograms, square meters of body surface area, kilograms of lean body mass or another suitable measure.

Blood is then withdrawn at step 210 from patient 100 according to the expected rate of removal of ultrafiltrate from the blood stream and the selected dosage of ultrafiltrate removal and pumped to hemofilter 102 at step 212. Ultrafiltration of the blood using hemofilter 102 occurs at step 214. Filtered blood is preferably returned to patient 100 at step 216. Often treatment will be accomplished by continuous flow of blood, filtered blood and ultrafiltrate. However, periodic or intermittent hemofiltration may also be conducted in accordance with teachings of the present invention depending upon the patient's condition.

Fluid sieved from the blood by hemofilter 102 then enters an ultrafiltrate stream at step 218. The ultrafiltrate stream removed by hemofilter 102 may be measured to ensure that the selected dosage of ultrafiltrate is removed. If the volume of the blood entering the hemofilter is not in accord with the selected dosage of ultrafiltrate removal, the volume of blood removed and pumped to the hemofilter 102 may be selectively increased or decreased to produce the selected dosage of ultrafiltrate removal. All or a selected portion of the ultrafiltrate may be directed into the waste stream at step 220, where it is ultimately discarded at step 222.

Optional step 270 may also be included to recycle or clean the ultrafiltrate. Replacement fluid may be added at step 272 to the cleaned or recycled ultrafiltrate. The clean ultrafiltrate may be returned to the ultrafiltrate stream at step 224 or may be discarded at step 220.

The result of dose quantification and selection will be to assure equally intense hemofiltration-ultrafiltration treatment is provided to each subject receiving any given dose, regardless of body size. Dose will allow comparison of therapeutic regimens, duration, and hemofilters with respect to effectiveness, side effects, and costs.

Removal or exchange of target molecules, target receptor molecules, and target complex molecules depends on a number of variables. These variables include duration of therapy, membrane sieving coefficients for target molecules, target receptor molecules, and target complex molecules, and filter blood and ultrafiltrate flow rates, among others. Short duration (but intense) therapy can rapidly remove target molecules, target receptor molecules, and target complex molecules from plasma, but may leave insufficient time for target molecules, target receptor molecules, and target complex molecules to move from tissue sites into plasma, thus limiting the total body reduction of target molecules. Longer treatment times will allow for movement of target molecules from tissues, but, if sieving coefficient is excessively high, then plasma colloid replacement fluid would not be efficiently used. Filter blood and ultrafiltrate flow will also materially affect efficiency of treatment. Appropriate treatment duration will depend on the nature of the pathophysiologic condition to be treated, its severity, and other relevant clinical factors as assessed by a physician. Thus, the combinations of treatment duration, sieving coefficient, and filter blood and ultrafiltrate flow will vary.

A sieving coefficient approaching (or even exceeding) 1.0 for target complex molecules (or other target molecules) may often provide the most efficient removal of target molecules, and in certain circumstances will be most desirable. Sieving coefficients for target complex molecules (and target molecules) above 0.5 will also be reasonably effective. Lower sieving coefficients (between about 0.05 and 0.5) may provide sufficiently effective sieving under certain treatment circumstances. Sieving coefficients that are too low either initially or after membrane polarization are considered inadequate for VLPH.

The sieving characteristics of membrane pores depends not only on the nominal pore size, but also on the physical, chemical, and electrical characteristics of the material from which it is made and the particular manufacturing technique used to produce the membrane. As a result, the sieving coefficient for albumin and other target receptor molecules, and target molecules, may vary among membranes with the same nominal pore size. However, the nominal molecular weight cutoff to provide adequate sieving of target receptor molecules, target complex molecules, and target molecules, is expected to be approximately 150,000 to 500,000 Dalton. Very large pore hemofilter 102 will typically have pores with a molecular weight cutoff substantially less than that of plasmapheresis filters, so that no significant amount of immunoglobulins and similar large molecules will be sieved from the blood.

A 150-500 kD very large pore hemofilter may be used to accomplish plasma colloid exchange therapy (PCET) in accordance with teachings of the present invention. The very large pore hemofilter may filter patient blood with post filter blood returning to patient 100 and ultrafiltrate containing plasma water, target complex molecules, target receptor molecules, and target molecules, discarded to waste reservoir 119 at step 222. Alternatively, all or portions of the ultrafiltrate may be cleaned and recycled back to patient 100 at steps 270, 224 and 226. Sieving albumin and other target complex molecules, should have the intended effect of rapidly reducing target molecules, but will also rapidly deplete plasma albumin and other target receptor molecules. Therefore, an infusion into the patient of plasma colloid replacement fluid (see below) will be administered in sufficient quantity to accomplish two goals. First, to maintain a serum albumin sufficient to preserve adequate plasma oncotic pressure. Second, to provide fresh albumin and/or other target receptor molecules, with binding sites unoccupied by IM and/or toxins, which can attract target molecules from tissue spaces and tissue binding sites, and subsequently clear target molecules through the very large pore hemofilter.

The continuous exchange of fresh albumin and other target receptor molecules, with its broad distribution through the circulation, should allow intravascular binding kinetics favorable to the removal of target molecules from tissue sites. The dwell time of fresh albumin and/or other target receptor molecules in the body should allow saturation of the target receptor molecules, and make for efficient use of target receptor molecules. In this manner, removal of target molecules from blood and tissue can be accomplished in IMRD, liver failure, exogenous intoxication, and other conditions associated with toxins in the blood.

As with all hemofiltration procedures, a replacement fluid will be needed. Current replacement fluids are often crystalloid only, consisting of pharmaceutical grade, balanced salt solutions. The present invention teaches a plasma colloid replacement fluid ("PCRF") which includes pharmaceutical grade balanced salt solution containing albumin and/or other target receptor molecules and/or other physiologic molecules in a sufficient concentration to adequately replenish ongoing losses. For example, the concentration of albumin could range from 0.5 gm/100 ml to 10.0 gm/100 ml and would be operator determined. The concentration of other target receptor molecules would be operator determined. Whether to include specific target receptor molecules, the selection and amounts of target receptor molecules, are operator dependent.

PCRF will be used as all or part of the replacement fluid in the plasma colloid exchange therapy. PCRF may be added to the blood circulation at any point, but preferably in the post dilution mode in the very large pore hemofilter circuit. For example see step 250 in FIG. 2. The plasma colloid exchange therapy may be used in a single pass mode, with discard of filtrate, and infusion of PCRF. Alternatively, plasma colloid exchange therapy may be done in a filtrate recycling mode (See step 272) with recycling of filtrate through a recycling system so that all or part of the ultrafiltrate may be returned to the mammal. PCRF may also be infused during the recycling.

For the embodiment of the present invention as shown in FIG. 1, system 90 includes replacement fluid source 150. Plasma colloid replacement fluid may be supplied by replacement fluid source 150. For the embodiment shown in FIG. 1, replacement fluid source 150 includes fluid reservoir 152, tubing 154 and control valve 156. Various types of intravenous bags or other containers may be used as reservoir 152.

For this particular embodiment, tubing 154 is coupled with tubing 129 between ultrafiltrate pump 106a and three-way joint 110. Reservoir 152 preferably includes at least one port which may be coupled with tubing 154 to supply PCRF from reservoir 152 to tubing 129. Control valve 156 may be used to regulate the flow rate of PCRF in accordance with teachings of the present invention. Additional PCRF may also be added to reservoir 152 using this same port or another port (not expressly shown).

For some applications replacement fluid source 150 may be generally described as a replacement fluid kit. Multiple replacement fluid kits may be maintained in the vicinity of hemofilter 102. For example, each replacement fluid kit may include a respective reservoir 152 filled with different types of PCRF. An appropriate connector (not expressly shown) may also be provided to allow quickly engaging and disengaging reservoir 152 with tubing 154. For other applications, tubing 154 may be provided as part of each replacement fluid kit. An appropriate connection (not expressly shown) may be provided to couple tubing 154 with tubing 129 or with other portions of the extra corporeal blood circuit associated with hemofilter 102.

Although the present invention has been described with respect to a specific preferred embodiment thereof, various changes and modifications may be suggested to one skilled in the art and it is intended that the present invention encompass such changes and modifications fall within the scope of the appended claims.

What is claimed is:

1. A method for removing toxic substances from the blood of a patient, the method comprising:
    providing a system comprising:
        means for withdrawing blood from the patient;
        means for delivering the blood to a hemofilter having pores, the hemofilter having a molecular weight cut-off of greater than 150,000 Daltons and less than 1,000,000 Daltons so as to create a return stream and an ultrafiltrate stream, wherein the return stream has retained molecules that did not pass through the pores and the ultrafiltrate stream having molecules, including albumin and excluding significant amounts of immunoglobulins, that passed through the pores;
        means for removing at least a portion of the ultrafiltrate, so as to remove toxic substances contained in the ultrafiltrate from the blood;
        means for returning the return stream to the patient; and
        means for providing fluids to the patient that contain clean target receptor molecules, including albumin, to the patient; and
    conducting plasma colloid exchange therapy to the patient with the system sufficient to maintain plasma oncotic pressure of the patient and to provide fresh albumin optionally with other target receptor molecules to attract target molecules from tissue spaces in the patient.

2. The method according to claim 1, wherein the molecular weight cutoff is a nominal molecular weight cutoff.

3. The method according to claim 1, wherein the clean target receptor molecules consist of albumin.

4. The method according to claim 1, wherein the clean target receptor molecules consist of albumin and another substance.

5. The method according to claim 4, wherein the other substance is a specific target receptor.

6. The method according to claim 1, wherein the means for providing the fluid includes means for delivering albumin in an amount sufficient to maintain adequate oncotic pressure.

7. The method according to claim 1, further comprising means for removing all of the ultrafiltrate.

8. The method according to claim 1, further comprising means for cleaning and returning at least a portion of the ultrafiltrate.

9. The method according to claim 8, wherein the means for cleaning includes an adsorbent material.

10. The method according to claim 1, wherein the means for removing includes means for removing a predetermined amount of ultrafiltrate based on one of the body size of the patient, the time of therapy, and the rate of flow of blood to the hemofilter.

11. The method according to claim 1, wherein the means for removing includes means for adjusting the rate of ultrafiltrate removal by altering the rate of delivering blood to the hemofilter.

12. The method according to claim 1, wherein the means for providing the fluids includes a line for delivering the fluid to the patient.

13. The method according to claim 12, wherein the means for providing the fluids includes means for providing the fluid concurrently with removing at least a portion of the ultrafiltrate.

14. The method according to claim 1, further comprising means for infusing the fluids directly into the patient.

15. The method according to claim 1, further comprising means for infusing the fluids into a blood circuit associated with the hemofilter.

16. The method according to claim 1, further comprising means for providing an ultrafiltration rate of between 2 and 20 liters per hour.

17. The method according to claim 1, further comprising means for providing an ultrafiltration rate of between 6 and 12 liters per hour.

18. The method according to claim 1, wherein the step of conducting plasma colloid exchange therapy comprises treating at least one of the following:
    inflammatory mediator related disease (IMRD), liver failure, and exogenous intoxication.

* * * * *